United States Patent
Berier et al.

(10) Patent No.: US 8,577,445 B2
(45) Date of Patent: Nov. 5, 2013

(54) MINIATURE CONFOCAL OPTICAL HEAD WITH INTEGRATED SCANNING AND CONFOCAL IMAGING SYSTEM USING SAME

(75) Inventors: Frederic Berier, Courbevoie (FR); Bertrand Viellerobe, Nogent sur Marne (FR); Magalie Genet, Guyancourt (FR); Francois Lacombe, Chaville (FR); Pedro Santos, Saint Pierre les Nemours (FR)

(73) Assignee: Mauna Kea Technologies, Paris (FR)

( * ) Notice: Subject to any disclaimer, the term of this patent is extended or adjusted under 35 U.S.C. 154(b) by 962 days.

(21) Appl. No.: 10/539,519

(22) PCT Filed: Dec. 12, 2003

(86) PCT No.: PCT/FR03/03686
§ 371 (c)(1),
(2), (4) Date: Jun. 17, 2005

(87) PCT Pub. No.: WO2004/066016
PCT Pub. Date: Aug. 5, 2004

(65) Prior Publication Data
US 2006/0056017 A1    Mar. 16, 2006

(30) Foreign Application Priority Data
Dec. 20, 2002 (FR) .................... 02 16279

(51) Int. Cl.
*A61B 5/05* (2006.01)
(52) U.S. Cl.
USPC ........... 600/425; 600/101; 600/407; 600/196; 600/109; 359/211.1; 359/212.1; 359/214.1

(58) Field of Classification Search
USPC .............. 600/407, 100, 160, 101, 109, 425; 359/196–215, 220–221, 211.1–226.3
See application file for complete search history.

(56) References Cited

U.S. PATENT DOCUMENTS

| | | | |
|---|---|---|---|
| 5,742,419 A | 4/1998 | Dickensheets et al. | |
| 5,907,425 A | 5/1999 | Dickensheets et al. | |
| 6,007,208 A | 12/1999 | Dickensheets et al. | |
| 6,057,952 A | 5/2000 | Kubo et al. | |
| 6,088,145 A | 7/2000 | Dickensheets et al. | |
| 6,091,067 A * | 7/2000 | Drobot et al. | 250/234 |
| 6,154,305 A * | 11/2000 | Dickensheets et al. | 438/24 |

(Continued)

FOREIGN PATENT DOCUMENTS

| | | |
|---|---|---|
| WO | WO 99/00690 | 1/1999 |
| WO | WO 00/16151 | 3/2000 |
| WO | WO 02/13343 | 2/2002 |

*Primary Examiner* — Joel Lamprecht
(74) *Attorney, Agent, or Firm* — Osha Liang LLP

(57) ABSTRACT

An optical head includes: a point source producing an excitation beam, optical elements adapted to converge the optical beam into an excitation point located in a subsurface plane relative to the surface of a sample, the plane being perpendicular to the optical axis of the optical head; and elements for scanning the excitation point so as to define an observation field in the subsurface plane along two perpendicular scanning directions, a rapid online scanning and a slow columnar scanning. The invention includes micro-electrical mechanical systems designed to move in translation along a selected displacement at least one of the optical elements, which is mobile along a direction perpendicular to the optical axis so as to obtain at least one of the scanning directions. The invention provides the advantages of maintaining an axial illumination of the sample and of using a miniature head.

22 Claims, 2 Drawing Sheets

(56) References Cited

U.S. PATENT DOCUMENTS

| | | |
|---|---|---|
| 6,172,789 B1 | 1/2001 | Kino et al. |
| 6,498,685 B1 * | 12/2002 | Johnson .................... 359/626 |
| 6,639,201 B2 * | 10/2003 | Almogy et al. ............ 250/208.1 |
| 6,640,124 B2 * | 10/2003 | Elsner et al. ................ 600/407 |
| 6,841,787 B2 * | 1/2005 | Almogy .................. 250/492.24 |
| 6,897,941 B2 * | 5/2005 | Almogy ........................ 355/67 |
| 6,975,898 B2 * | 12/2005 | Seibel ........................ 600/473 |
| 7,113,651 B2 * | 9/2006 | Liang ......................... 382/284 |
| 7,130,115 B2 * | 10/2006 | Olszak et al. ................ 359/372 |
| 7,221,824 B2 * | 5/2007 | Berier et al. .................. 385/33 |
| 2001/0046712 A1 * | 11/2001 | Hang et al. .................. 436/172 |
| 2002/0018276 A1 | 2/2002 | Suga |
| 2003/0076571 A1 * | 4/2003 | MacAulay et al. .......... 359/237 |
| 2003/0130562 A1 * | 7/2003 | Barbato et al. .............. 600/109 |

\* cited by examiner the axial direction of the fibre and the other in the direction perpendicular to the optical axis. The positioners, in order to offer an appropriate displacement relative to the field of view, must have a given length. Perpendicular to the axis of the optical fibre, this length constraint in fact leads to an optical head diameter too large for the in vivo applications in situ according to the present invention.

MINIATURE CONFOCAL OPTICAL HEAD WITH INTEGRATED SCANNING AND CONFOCAL IMAGING SYSTEM USING SAME

BACKGROUND OF THE INVENTION

1. Field of the Invention

The present invention relates to a confocal optical head, in particular miniature, comprising integrated beam scanning means and a confocal imaging system equipped with said head.

More precisely, the present invention relates to an optical head and a corresponding optical system, in which a field to be imaged in a specimen is scanned point by point by an excitation signal. This type of system makes it possible to obtain, by means of data processing, a confocal image constructed point by point in real time. The confocal character is obtained by means of spatial filtering making it possible to detect a return signal originating solely from the excited point of the specimen taking the same optical path as the excitation signal.

2. Description of the Related Art

One of the intended fields of application is that of high resolution confocal imaging, making it possible to observe and analyze a biological tissue in vivo, in situ, in real time, in particular accessible via the operating channel of an endoscope or integrated into the endoscope. The invention can also be applied to the fields of dermatology or gynaecology requiring less advanced miniaturization of the optical head. It can also be applied to the field of electronics for example for the control of semi-conductors or similar materials.

According to a first type of system, in particular described in the Patent Application WO 00/16151, an image guide is used, constituted by a bundle of flexible optical fibres, comprising at its distal end an optical focusing head intended to come into contact with the specimen to be analyzed. The excitation beam scanning means are situated at the proximal end of the image guide provided for scanning the fibres in turn. The confocal character resides here, in particular, in the fact that the same optical fibre of the guide is used to convey the excitation signal and the return signal emitted. This type of system has the advantage of an optical head simplified from the mechanical point of view and thus essentially comprising optical focusing means which can be miniaturized. On the other hand, it has certain drawbacks, linked to the use of an array of optical fibres, in particular, the problem of sampling the tissue (continuity between the excitation points corresponding to the illumination of a fibre), the problem of injecting the fibres one by one and of the parasitic reflections at the inlet and outlet of the image guide, the sophisticated data processing of the image necessary in order to then correct the pattern of the fibres on the image, etc.

According to another known type of system, the beam scanning means are situated in the optical head at the distal end of an image guide comprising a single flexible optical fibre. The confocal character is obtained here due to the fact that the optical fibre is used for conveying the excitation signal and return signal emitted with an appropriate core diameter of the fibre.

The drawbacks of this type of system are then essentially linked to difficulties of miniaturizing the head, reproducibility and reliability of the mechanical means used for carrying out the scanning of the emergent beam of the optical fibre.

The document U.S. Pat. No. 6,091,067 describes a scanning system in which an optical fibre is fixed to two bimorphic piezoelectric positioners, one of the positioners is placed in the axial direction of the fibre and the other in the direction perpendicular to the optical axis. The positioners, in order to offer an appropriate displacement relative to the field of view, must have a given length. Perpendicular to the axis of the optical fibre, this length constraint in fact leads to an optical head diameter too large for the in vivo applications in situ according to the present invention.

Several documents describe confocal miniature optical heads using micro-mechanical-type micro-mirrors (MEMs).

The Patent Application U.S. 2002/0018276 describes a miniature confocal system using an optical fibre. The light leaving the fibre is reflected on the metallized part of a lens. This light is then reflected on a two-dimensional MEMs micro-mirror surrounding the fibre. The light is then sent towards the specimen via an optical system. The light returning from the specimen follows the reverse path and returns by the fibre which serves for spatial filtering. The system is miniature, being 2 mm in diameter and 2.5 mm in length.

The patents U.S. Pat. No. 6,154,305, U.S. Pat. No. 6,088,145, U.S. Pat. No. 6,007,208, U.S. Pat. No. 5,907,425 and U.S. Pat. No. 5,742,419, describe a confocal head in which the scanning of the field of view is carried out by two electrostatically pivoted MEMs micro-mirrors. The proposed head can be miniaturized but on the other hand offers a 60×60 μm field of view which is too small with respect to the applications according to the invention corresponding to a field measuring 100×100 μm minimum in order to be able to observe, for example, several nuclei which are 5 μm in diameter generally spaced out at intervals of several tens of μm. The number of images per second of 5 to 8 is moreover also insufficient for imagery in real time (requiring a minimum of 10 to 12 images per second in the slowest mode with 640 lines). Moreover also, the field of view is situated parallel to the axis of the optical fibre, which can lead to practical difficulties of use (correct positioning of the probe).

The patents U.S. Pat. No. 6,172,789 and U.S. Pat. No. 6,057,952 describe a confocal optical head with a field of view this time in the axis of the optical fibre and allowing adjustment of the depth of the observation plane. The scanning means include a mobile mirror and a fixed mirror. The mobile mirror has an opening in its centre, and is of MEMs type, mounted so as to be able to pivot at least in one direction. The reflection surfaces of the mobile and fixed mirrors are situated face-to-face. The light leaving the optical fibre passes through the opening in the mobile mirror, then is reflected by the fixed mirror in the direction of the mobile mirror.

The following drawbacks in particular are encountered with such a head construction: significant cost of the mobile mirror with a hole in the centre, and also the scanning speed of such a two-dimensional MEMs mirror which is not sufficient for imagery in real time.

Generally, the change in direction of the optical beam by successive reflections on micro-mirrors leads to optical faults which are complicated to correct, in particular distortion or field curvature.

SUMMARY OF THE INVENTION

The purpose of the present invention is to overcome these drawbacks and propose an optical head which is of high resolution, confocal (offering an axial optical resolution of approximately 1 to 2 μm) and which comprises scanning means integrated with an excitation beam. According to other objectives, the optical head must be able to be miniaturized (not exceeding 3 mm in diameter in total), to make it possible to produce an image in real time (at least 10 images/second)

and to cover a field to be imaged of the order of 100×100 µm minimum and preferably 150×150 µm.

It proposes a miniature confocal optical head for a confocal imaging system, in particular endoscopic, said head comprising:

a point source producing an excitation beam;

optical means capable, in particular, of causing said optical beam to converge into an excitation point situated in a subsurface plane relative to the surface of a specimen, said plane being perpendicular to the optical axis of the optical head; and means of scanning said excitation point so as to describe a field of view in said subsurface plane in two perpendicular scanning directions, rapid line scanning and slow column scanning, characterized by MEMs mechanical micro-system means capable of moving in translation according to a chosen displacement at least one of the optical means which is mobile in a direction perpendicular to said optical axis so as to obtain at least one of said scanning directions.

According to the invention, lateral beam scanning is carried out by moving laterally relative to the optical axis one of the transmission optics, the optical axis of the optical head is thus modified only laterally and non-angularly as with reflection optics. This has the advantages of preserving an axial illumination of the specimen and minimizing the diameter of the optical head.

The mechanical micro-system means belong to the family of micro-components, known by the generic name of MEMs, making it possible to carry out scanning operations, switches, deflections (in particular of mirrors) etc., actuated by the pulse generally of an electric field.

The MEMs means which can be used according to the invention are in particular the following:

electrostatic actuators using the attractive force between two charges;

thermal actuators using a temperature gradient or the difference in thermal dilatation coefficient between two materials, an electric current creating for example a rise in temperature;

magnetic actuators using the force resulting from the interaction of two magnetic fields; generally, a field external and a field internal to the MEMs are applied, for example a coil creating an external field when an electric current passes through it.

The MEMs have a response time compatible with the movement of an optical means, in particular a lens, over a distance, allowing for magnification, corresponding to the dimension of the field to be imaged according to the invention, namely of the order of 150 µm, and at a speed allowing a choice of slow scanning comprised between approximately 10 and 15 Hz, corresponding to column scanning of the field to be imaged, or rapid scanning of approximately 4 kHz, corresponding to line scanning of the field. The MEMs moreover have dimensions compatible with a miniaturization of the optical head, of the order of 2 to 3 mm in total diameter, as shown by the detailed description given hereafter. They make it possible to impart a stable and repeatable movement of the optics. Preferably, to this end, the MEMs means used according to the invention are constituted by means of movement, for example pairs of electrostatic combs, arranged in a diametrically opposite manner and actuated according to different modes, simultaneously or alternately. Other MEMs systems also exist in the form of a ring in the opening of which a lens can be fixed and also operating alternately in order to impart a reciprocating translation movement.

The point source can be of fibre type, and therefore offset: the end of a flexible optical fibre connected to a laser source is fixed to the optical head. The source can also be constituted by a VCSEL (Vertical-Cavity Semiconductor Emitting Laser) component which is virtually a point laser source having a cavity the outlet of which measures a few microns in diameter. In both cases, the dimension of the source (core diameter of the optical fibre or diameter of the outlet of the cavity of the VCSEL component) is chosen in order to be able to serve as a filtering hole of the backscattered signal and to produce a confocal image. If a VCSEL source is used, a detector is placed just behind the cavity in order to construct the detection route. Moreover, the numerical aperture of the source, fibre type or VCSEL type, is chosen in order to collect the maximum amount of photons emitted by each excitation spot, typically comprised between 0.2 and 0.4.

The optical means used in the optical head generally comprise first optical means, placed at a chosen focal distance from the point source, capable of transforming the excitation beam emitted from the source, which is divergent because of the numerical aperture of the source, to a parallel or slightly divergent beam. These optical means are constituted by a lens or by a set of refractive (standard or with an index gradient) and/or diffractive lenses. Diffractive lenses have the advantage of being smaller and lighter. Second optical means placed at a chosen focal distance from the first optical means then have the function of focusing the optical beam into an excitation point situated in the subsurface observation plane. These optical means can also be constituted by a lens or by a set of refractive and/or diffractive lenses.

Preferably, MEMs means are utilized according to the invention for displacing the first optical means rather than the second optical means and at a frequency making it possible to carry out slow column scanning. The scanning of the second optical means would lead to additional optical aberrations because of their large numerical aperture on the specimen.

As regards rapid line scanning, according to the invention, the latter can be carried out either by moving the source, using for example suitable piezoelectric means, or with a fixed source and movement of the second optical means also using appropriate MEMs means and in a direction perpendicular to the movement of the first optical means.

Additional scanning in the z direction, in order to modify the depth of visualization, can moreover be provided in the optical head according to the invention, for example using MEMs means capable of moving the mobile optical means along the optical axis of the optical head, or using means capable of modifying the radius of curvature of one of the optical means, preferably that closest to the specimen. Such scanning advantageously makes it possible to re-create a 3D image by data processing.

The present invention also proposes a confocal imaging system using an optical head as defined above. According to a first example, the system comprises a fibre-type source. According to a second example, it comprises a VCSEL-type source associated with detection means integrated in the optical head and flexible linking means between said head and the signal data processing means.

BRIEF DESCRIPTION OF THE DRAWING FIGURES

The present invention will be better understood and other advantages will appear more clearly in light of the following description of embodiments, a description made with reference to the attached drawings in which.

DETAILED DESCRIPTION OF THE PREFERRED EMBODIMENTS

Figure 1:
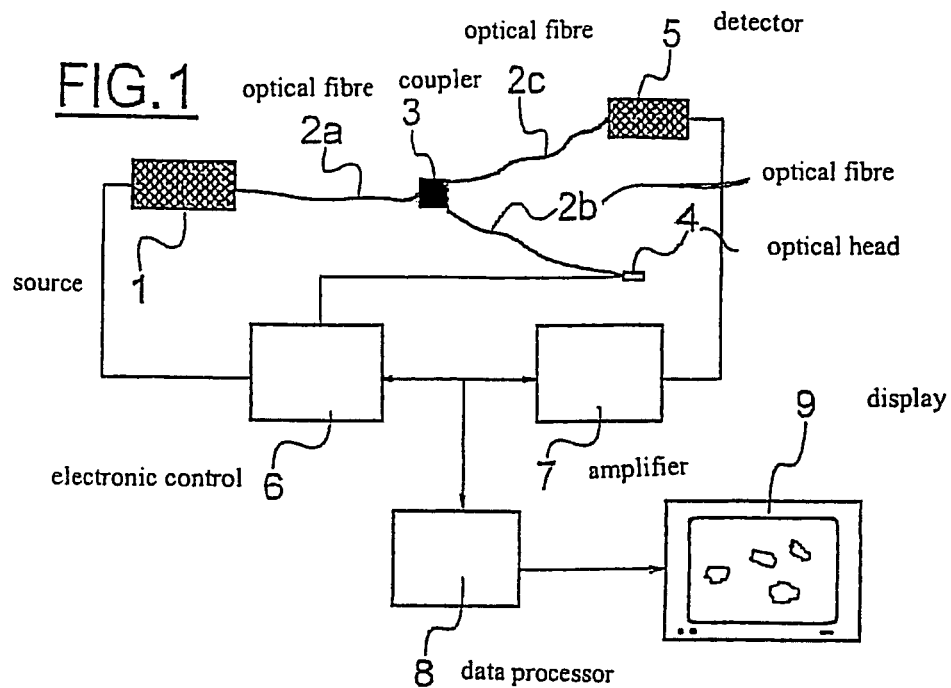
FIG. 1 is a general diagram of an example of a fibre-type confocal imaging system using the miniature head according to the invention.

FIG. 1 schematically represents a fibre-type confocal imaging system which can include a miniature head according to the invention.

The system comprises a source 1, for example a laser source, capable of emitting an excitation signal with a wavelength capable of generating in a specimen a return fluorescence or backscattering signal, said signal being conveyed by a first single-mode optical fibre 2a to coupling means 3, for example a 50/50 fibre coupler, provided in order to direct the excitation signal originating from the source 1 into a single-mode optical fibre 2b at the end of which the miniature optical head 4 according to the invention is situated and in order to direct the return signal originating from the excited site towards detection means 5, for example a photodetector, using a third single-mode optical fibre 2c. The system comprises electronic control, command and synchronization means 6, making it possible to control the source 1, the scanning means of the optical head 4 and the detection means 5, in a synchronized manner, in order in particular to know the location of the signal in the specimen in order to allow the construction of an image in real time. The system moreover comprises electronic means 7, of amplification, forming and A/D conversion of the signal detected by the detection means 5, data-processing means 8 comprising an acquisition card and a graphics card and means of displaying 9 the images obtained.

This system operates overall in the following manner: the miniature optical head 4 is brought into contact with a specimen to be analyzed, for example via the operating channel of an endoscope. The source 1 sends an excitation signal with a chosen wavelength into the portion of fibre 2a. The coupler 3 directs the excitation signal into the portion of fibre 2b guiding the signal into the optical head 4 where it is scanned and focused on an analysis surface (or analysis field) in a plane of the specimen perpendicular to the optical axis defined by the optical fibre 2b, at a given depth in the specimen. A return signal originating from the scanned surface in the specimen follows the reverse path of the excitation signal as far as the coupler 3: it is picked up by the optical means of the optical head 4, recoupled in the portion of fibre 2b, then directed by the coupler 3 into the portion of fibre 2c towards the detector 5. The signal detected is amplified and converted to a digital signal, then subjected to data-processing in order to finally constitute an image element displayed in real time.

The miniature head according to the invention is now described in detail with reference to the chosen embodiment and represented in FIG. 2.

The head comprises, in a mechanical support structure 15:
piezoelectric-type means 11 to which is fixed the terminal portion of the optical fibre 2b, capable of moving this terminal part of optical fibre, and therefore the optical beam leaving the latter, approximately in reciprocating translation along a chosen displacement $D_L$, approximately perpendicular to the optical axis A defined by the optical fibre, and corresponding to a displacement on a line of the field to be imaged (these piezoelectric means are described hereafter in detail);

first optical means 12 capable of converting the beam leaving the fibre 2b which is diverged to a parallel or slightly divergent beam, and picking up the return beam originating from the specimen; these optical means are according to the invention mobile in translation, so as to move the optical beam along a chosen displacement, schematically shown by the double arrow, perpendicular to the displacement $D_L$, and corresponding to a column displacement of the field to be imaged;

MEMs-type micro-mechanical means, 14a and 14b, capable of reciprocally moving the optical means 12 along the displacement $D_L$ (these means are described hereafter in detail);

second fixed optical means 13 capable of causing said parallel beam to converge in order to focus it into a point or spot S in a plane P of the examined specimen E situated at a given depth and approximately perpendicular to the optical axis A.

The piezoelectric means 11 and the MEMs means 14a and 14b thus together make it possible to carry out the scanning of the beam focused on the field to be imaged, the piezoelectric means 11 serving to carry out a rapid line scanning and the MEMs means 14a and 14b serving to carry out slow column scanning.

The mechanical support structure 15 is constituted by a hollow body 16, for example a tubular optic holder, with, at one end, a light window 17, intended to come into contact with the specimen E, capable of being passed through by the excitation and return backscattering or fluorescence signals, and with, at its other end, a passage 18 for the terminal portion of the optical fibre 2b and also for the piezoelectric means 11. A side wall 19 surrounds the passage 18 in order to tightly seal the optical head. The fixed optical means 13 are fixed and centred relative to the optical axis A inside the body 16, and the mobile optical means 12 are linked to the inside face of the body 16 via the MEMs means 14a and 14b as explained hereafter in detail.

The optical fibre 2b coupled to the optical head is preferably single-mode, allowing the most homogeneous possible illumination of the specimen. The numerical aperture of the fibre is chosen to be as large as possible in order to allow an optimized collection of photons, and in order to allow, together with an appropriate core diameter, a coupling of the return signal in the fibre, and therefore spatial filtering, which is the best possible. Typically, the numerical aperture is 0.4 and the core diameter comprised between 1 and 2 μm. This choice of characteristics for the optical fibre, together with the characteristics of the optical means 12 and 13, make it possible to carry out spatial filtering of the return signal ensuring the confocality of the system.

According to the example chosen, the piezoelectric means 11 are constituted by a piezoelectric positioner having a surface on which is fixed, for example by gluing, the terminal part of the optical fibre 2b with an end portion of the protruding fibre. This positioner 11 is double, therefore called bimorphic, having the feature of being deformed when an electrical voltage is applied to it; this makes it possible to move the optical fibre between a non-excited or rest position of the positioner and an excited position corresponding to the excitation of the positioner. The positioner 11 is chosen so as to exhibit a displacement between these two positions, allowing for magnification, corresponding to the field width which is to be imaged in the specimen. Moreover, positioner 11 is chosen so as to be able to be excited at a frequency making it possible to carry out the desired rapid line scanning of the specimen. Moreover, for a positioner of given length, compatible at its maximum with miniaturization, a maximum scanning amplitude can be obtained by exciting the positioner at its resonant frequency. Typically, a positioner of 7.5 mm in length, excited with a sinusoidal excitation voltage of ±60V, makes it possible to achieve a resonant frequency of 4 kHz, making it possible to carry out line scanning at a speed appropriate to imaging in real time (at least 10 images/second), over a imaged field 150 μm in width (with unitary magnification). This length is compatible with the maximum total dimension for the head of approximately 30 mm. The width of the positioner (dimension perpendicular to the optical fibre) influences neither the resonance, nor the amplitude of scanning. Typically, the width of the positioner can be a few hundred microns, not exceeding the outside maximum total diameter provided for the head, approximately from 2 to 3 mm. In order to take account of a magnification greater than 1, for a given imaged field dimension, a longer piezoelectric positioner can be chosen in order to have a greater displacement and possessing a higher excitation voltage (±100V to 120V). The system moreover comprises the safety means necessary for the use of electrical voltages of this order for in vivo applications.

The MEMs means 14a and 14b serve to laterally move the mobile optical means 12 in a direction perpendicular to that of the movement of the fibre imparted by the piezoelectric means. More particularly according to the example chosen and represented in the figures, the mobile optical means 12 being constituted by a single lens, the MEMs means include two pairs of combs 14a and 14b, diametrically opposite, each pair of combs comprises one comb fixed to said lens 12 and one comb assembled with the body 16. The combs are semiconductor filaments which are aligned and the two combs in a pair have their filaments overlapping. The movement of the lens 12 is obtained by shifting one comb relative to the other by means of an electrostatic effect. The transversal movement achieved by means of the pairs of combs is perpendicular to the axis of the fibre. It is carried out at a slow frequency (typically from 10 to 15 Hz) and makes it possible to produce an imaged field size of 150 μm by choosing the appropriate scanning amplitude.

The mobile optical means 12 has the function of transforming the emergent divergent beam from the optical fibre 2b into a parallel or divergent beam. It must correspond to dimension constraints: its diameter must be compatible with a miniaturization of the head which must have a total external diameter of 2 to 3 mm maximum. It must correspond to mechanical constraints and be sufficiently solid and resistant to be able to be integral with the MEMs means 14 and actuated in translation. It must also correspond to optical constraints: its diameter must be sufficiently large relative to the diameter of the beam projected for the imaged field that is to be obtained (otherwise there is a risk of observing faults at the field edge (in particular vignetting)); the numerical aperture of the optical means 12 must be at least equal to or preferably greater than the numerical aperture of the fibre in order to preserve the confocality of the head and optimization of the number of photons detected during scanning. A minimum optical diameter of 1 mm can be obtained with a numerical aperture greater than 0.4 (numerical aperture of the optical fibre 2b), which is compatible with a miniature head 2 to 3 mm in outer diameter and the insertion of the MEMs means 14. By way of example, according to the most simplified mode, this optical means 12 is a standard lens but could also be a doublet of lenses or any other usual optical means making it possible to preserve a size and weight compatible with the sought objectives. As an example of more sophisticated optics, a diffractive lens can be used using diffraction in order to decompose the wave front of the incident beam on different zones and which after recombination makes it possible to obtain the sought wave front. Moreover, these optics have the advantages of a large numerical aperture, a small space requirement, low weight and low cost.

The fixed optical means 13 must make it possible to focus the scanned beam onto a spot S at a certain depth in the specimen in a focusing plane and to collect a maximum amount of photons originating from each spot in this same focusing plane. The characteristics of these optical means (in particular the magnification and the numerical aperture) are defined taking account of the specifications of the optical fibre and mobile optical means 12 in order to ensure confocality for the whole of the system and also in order to minimize the optical aberrations which could be engendered by the scanning (distortion, instability, shifting of the mobile optical means with respect to the optical axis etc.).

The exit window 17 is the last interface situated between the optical head and the specimen. It has the function of protecting the optics, and
also of carrying out an index matching between the head and the specimen, in particular by means of a treatment of its external face for example for an index of 1.33 equal to that of water. The window can as a variant also be constituted by a lens having a refractive power function on the optical beam.

Figure 3:
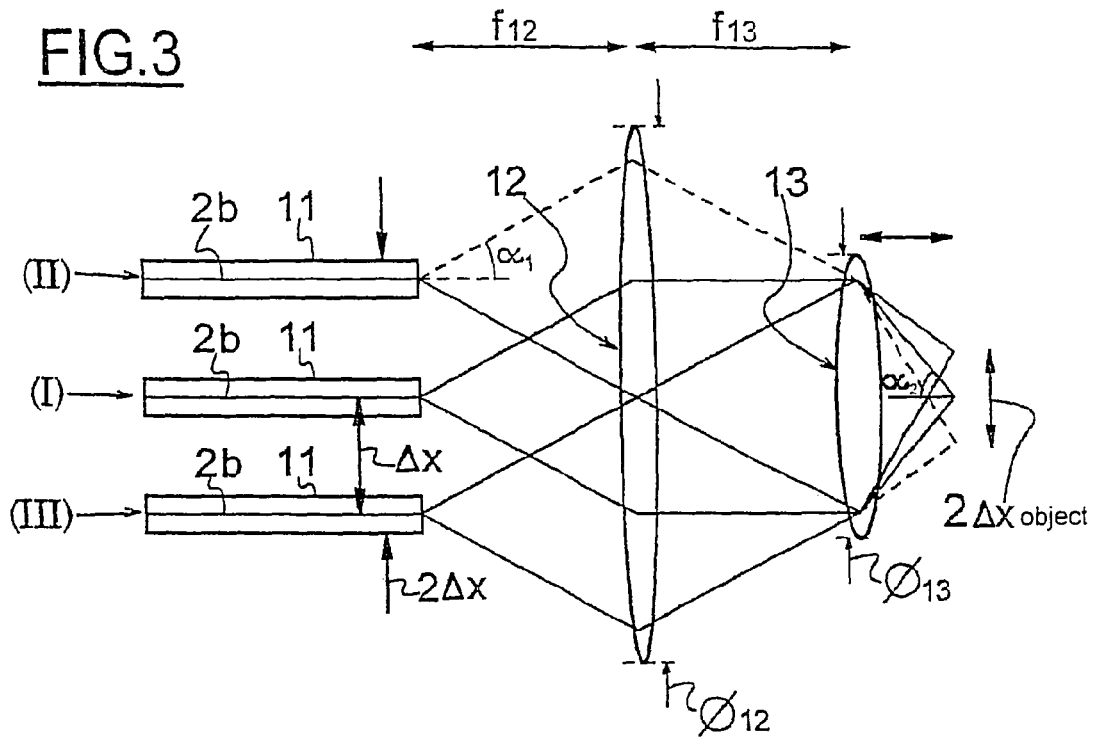
FIG. 3 is an optical diagram of the miniature head of FIG. 2.

FIG. 3 shows an optical diagram of the head which has just been described according to a possible particular example, illustrating in particular the line scanning of the specimen, on which the fibre 2b is represented in a standard fashion in its rest position I and in two extreme lateral positions II and III.

The optical specifications are the following:
scanned field: $2\Delta x = 400$ μm
core diameter of the fibre 2b: $\emptyset_{core} = 1.3$ μm
numerical aperture of the fibre 2b: numerical aperture=sin $(\alpha_1)=0.4$.
lens 12: diffractive
focal length of the mobile lens 12: $f_{12}=1.83$ mm
total diameter of the lens 12: $\emptyset_{12}=2$ mm
lens 13: diffractive
focal length of the fixed lens 13: $f_{13}=0.73$ mm
total diameter of lens 13: $\emptyset_{13}=1.6$ mm
magnification of the optical system=G=2.5
imaged field=$2\Delta x$ object=160 μm
numerical aperture object=numerical aperture object=n sin $(\alpha_2)=1$ (in water n=1.33)
diameter of each spot S focused in the specimen: limited by diffraction over the whole imaged field.

In the example which has just been described, the rapid line scanning means of the excitation spot are produced using a piezoelectric positioner to which the end of the optical fibre is fixed. According to a
possible embodiment variant, the optical fibre is fixed and the lens 13 is mobile, MEMs means, similar to the means 14a and 14b, being used in order to move the optical lens 13 in a direction perpendicular to the movement of translation of the mobile optical means 12 and according to a frequency compatible with rapid line scanning (4 KHz). Also as a variant, conversely, rapid scanning can be carried out by moving the lens 12 and slow scanning by moving the lens 13.

Figure 2:
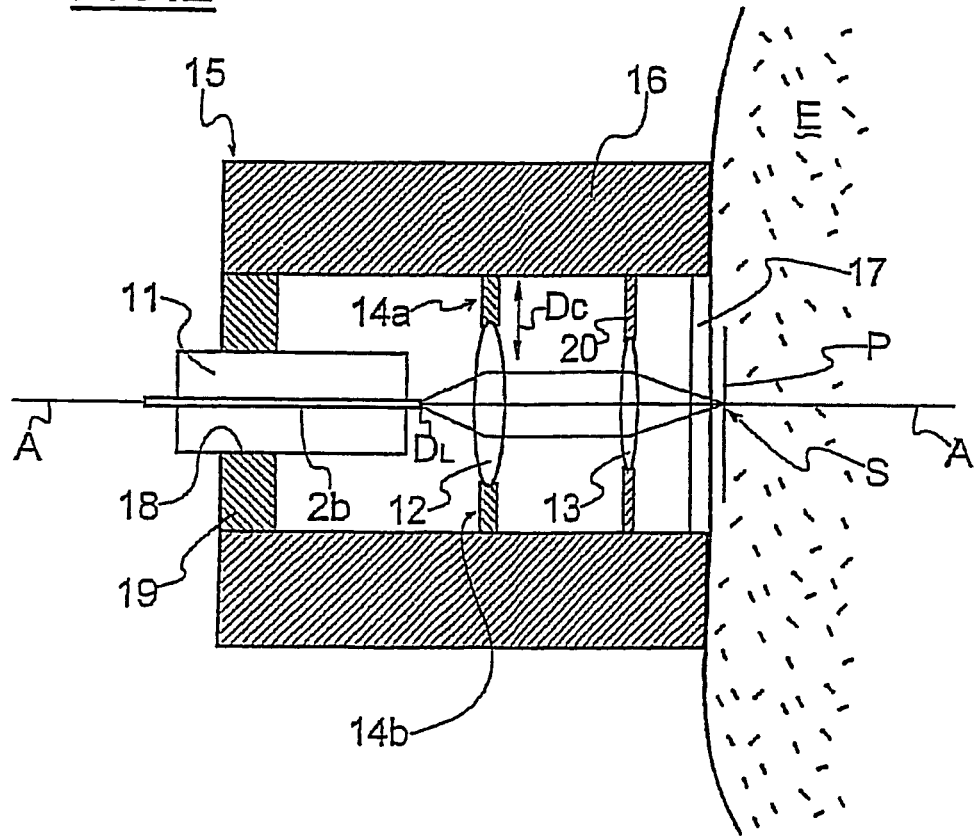
FIG. 2 is a side cross-section of a miniature head according to a first embodiment.
Figure 4:
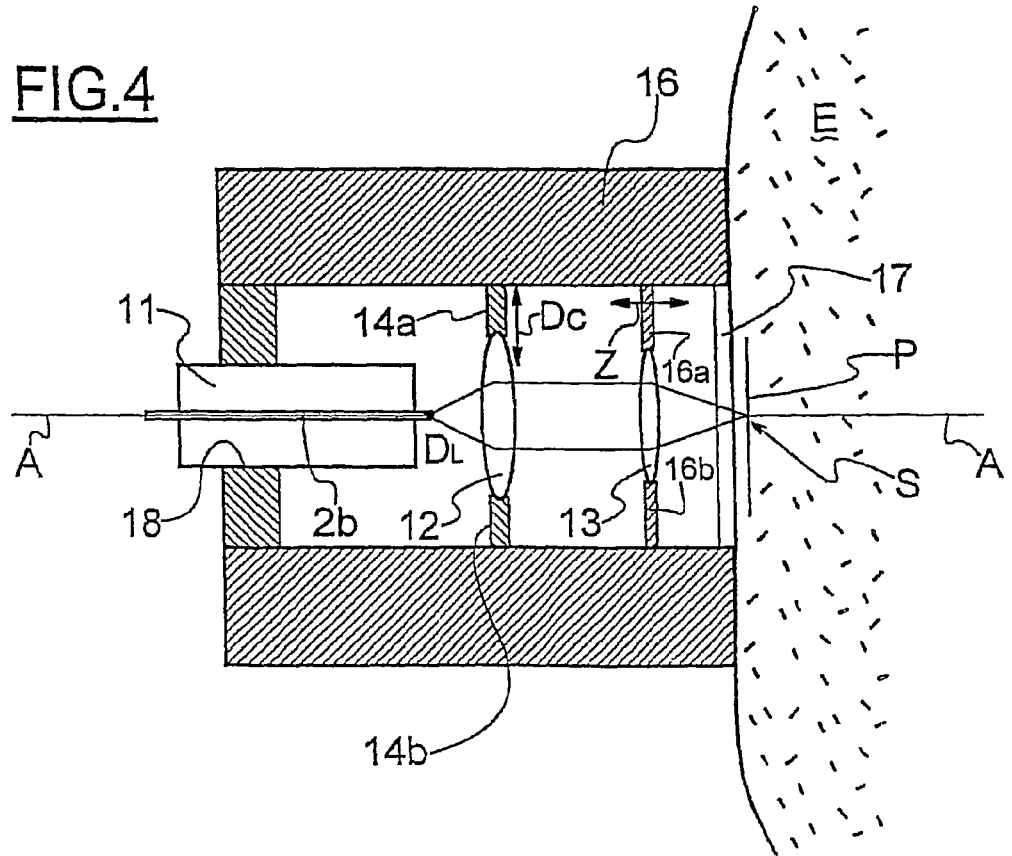
FIG. 4 is a view similar to FIG. 2 illustrating a second possible embodiment.

FIG. 4 also shows an embodiment variant of the optical head of FIG. 2, the identical means having the same references as in FIG. 2. In this variant, means 16a and 16b, fixed on one side to the tubular optic holder 15 and on the other to the lens 13, are used to move said lens 13 along the optical axis A of the head, making it possible to adjust the depth of visualization in the specimen, approximately over a few tens of μm, schematically shown by the double arrow Z. This advantageously makes it possible to produce three-dimensional reconstructions of the specimen which is observed: different two-dimensional data acquisitions are made at different depths and it is then possible to reconstruct the observed volume by data processing. In other cases, the adjustment of the depth of visualization can make it possible to advantageously adapt to the specimen observed, at the optimum depth of visualization of the specimen. The movement of the optical means 13 in the axial direction of the head makes it possible to cause the beam to converge at a different distance. The means 16a, 16b are of MEMs or piezoelectric type.

Also as an embodiment variant, the optical head can comprise instead of the optical fibre 2b a VCSEL-type point source associated with a detector placed just behind the cavity of the VCSEL. By way of example, with reference to FIG. 3, the following optical specifications can be given:

field scanned: $2\Delta x = 400\text{-}600$ μm
diameter of the opening of the VCSEL cavity: $\emptyset_{cavity} = 2\text{-}4$ μm
numerical aperture of the VCSEL cavity: numerical aperture=$\sin(\alpha_1)=0.25$ (in air)
lens 12: diffractive
focal length of the mobile lens 12: $f_{12}=3$ mm
total diameter of the lens 12: $\emptyset_{12}=2$ mm
lens 13: diffractive
focal length of the fixed lens 13: $f_{13}=1.17$ mm
total diameter of lens 13: $\emptyset_{13}=1.6$ mm
magnification of the optical system=G=3-imaged field=$2\Delta x$ object=160-240 μm
numerical aperture object=NA object=$n \sin(\alpha_2)=0.75$ (in water n=1.33)
diameter of each spot S focused in the specimen: limited by diffraction over the whole imaged field.

The invention claimed is:

1. A miniature confocal optical head for a confocal imaging system, or for an endoscopic confocal imaging system, said head comprising:
a point source for producing an excitation beam;
an optical system comprising a first optical device and a second optical device capable of causing said excitation beam to converge at an excitation point situated in a subsurface plane in a specimen, said plane being perpendicular to an optical axis of the optical head, wherein the optical head has a diameter less than or equal to 3 mm and a length of 30 mm; and
a scanning mechanism for scanning said excitation point so as to describe a field of view between 100×100 micrometers and 240×240 micrometers in said subsurface plane in two perpendicular scanning directions, wherein the scanning mechanism comprises a rapid line scanning device and a slow column scanning device, wherein at least one of the rapid line scanning device and the slow column scanning device comprises a micro-electro-mechanical system (MEMS) capable of moving at least one of the first optical device and the second optical device in a direction perpendicular to said optical axis.

2. The optical head according to claim 1, wherein the slow column scanning device operates at a frequency between 10 and 15 Hz and the rapid line scanning device operates at a frequency of about 4 kHz, so as to produce an image in real time.

3. The optical head according to claim 1, wherein the MEMS is capable of alternately moving, diametrically oppositely, the first optical device or the second optical device.

4. The optical head according to claim 1, wherein the excitation beam produced by the point source is divergent, the first optical device is capable of transforming said divergent beam into a parallel or differently divergent beam and the second optical device is capable of forming the subsurface focusing point.

5. The optical head according to claim 4, wherein the first optical device is mobile, capable of carrying out optical beam slow column scanning.

6. The optical head according to claim 1, wherein the first and second optical devices are mobile, each capable of being moved in a direction perpendicular to the optical axis so that each defines a scanning direction.

7. The optical head according to claim 1, wherein the point source is mobile, fixed to a piezoelectric device capable of moving the excitation beam emitted by said point source with a displacement chosen so as to define a second scanning direction.

8. The optical head according to claim 7, wherein the second scanning direction and characteristics of the piezoelectric device correspond to rapid line scanning.

9. The optical head according to claim 8, wherein the piezoelectric device comprises a bimorphic piezoelectric positioner extending along the optical axis of the head, said point source being fixed on one face of said positioner at a front end of the positioner facing the first and second optical devices.

10. The optical head according to claim 1, further comprising a device for modifying a depth of the subsurface plane in the specimen.

11. The optical head according to claim 10, wherein the device for modifying the depth of the subsurface plane in the specimen comprises an MEMS capable of moving the second optical device along the optical axis of the optical head.

12. The optical head according to claim 11, wherein the MEMS is capable of moving the second optical device in order to carry out a movement along an optical axis of the excitation beam.

13. The optical head according to claim 10, wherein the device for modifying the depth of the subsurface plane comprise a device adapted for modifying a radius of curvature of one of the first and second optical devices.

14. The optical head according to claim 1, wherein the point source comprises an optical fibre capable of guiding an excitation signal from an external source, wherein an emergent beam from the optical fibre constitutes the excitation beam, wherein the optical fibre is used to bring the optical head within a distance of between zero and 100 microns from the field of view.

15. The optical head according to claim 14, wherein the optical fibre is single-mode with a core diameter adapted to allow spatial filtering of a return signal and therefore ensuring the confocality of the optical head, with maximized numerical aperture.

16. The optical head according to claim 1, wherein the point source is of Vertical-Cavity Semiconductor Emitting Laser (VCSEL) type, having a numerical aperture and a cavity outlet diameter compatible with a confocal system, and associated with a detector placed behind a cavity of the VCSEL.

17. The optical head according to claim 1, further comprising a light window at an outlet of the optical head that contacts the specimen and in order to carry out an index matching.

18. The optical head according to claim 17, wherein the light window has a refractive power function on a focused optical beam.

19. The optical head according to claim 1, wherein the optical system comprising the first and second optical devices has a numerical aperture at least equal to a numerical aperture of the point source.

20. A confocal imaging system comprising:
 the optical head of claim 1;
 a detector configured to detect an emitted signal; and
 an electronic and data processing unit configured for controlling system operation and for processing detected signals and reconstructing a confocal image of an imaged field.

21. The system according to claim 20, wherein the point source comprises a first optical fibre linked to a laser source and a coupling device for coupling said first optical fibre to a second optical fibre for conveying to and from the optical head and a third optical fibre for conveying the emitted signal to the detector.

22. The system according to claim 20, wherein the optical head comprises a VCSEL source and an integral detector, the system comprises a flexible linking device between the optical head and the electronic and data processing unit.

* * * * *